United States Patent [19]

Innerfield, deceased et al.

[11] 4,067,777

[45] * Jan. 10, 1978

[54] DETERMINATION OF HEPARIN IN THE BLOOD

[76] Inventors: Irving Innerfield, deceased, late of Tenafly, N.J.; by H. Jean Innerfield, executrix, 20 Knickerbocker Road, Tenafly, N.J. 07670

[*] Notice: The portion of the term of this patent subsequent to Oct. 12, 1993, has been disclaimed.

[21] Appl. No.: 686,196

[22] Filed: May 13, 1976

[51] Int. Cl.² .............................................. G01N 31/14
[52] U.S. Cl. .............................................. 195/103.5 R
[58] Field of Search ................ 195/103.5 R; 23/230 B

[56] References Cited

U.S. PATENT DOCUMENTS 3,853,710  12/1974  Innerfield ...................... 195/103.5 R

*Primary Examiner*—David M. Naff
*Assistant Examiner*—C. A. Fan
*Attorney, Agent, or Firm*—Blum, Moscovitz, Friedman & Kaplan

[57] ABSTRACT

Heparin in the blood is determined over a wide range of concentrations by measuring the clotting time of serum derived from a test specimen of blood when combined under standard conditions with thrombin and plasma solutions. The clotting time is then determined from an experimentally-established functional relationship between clotting time and heparin concentration.

6 Claims, 1 Drawing Figure

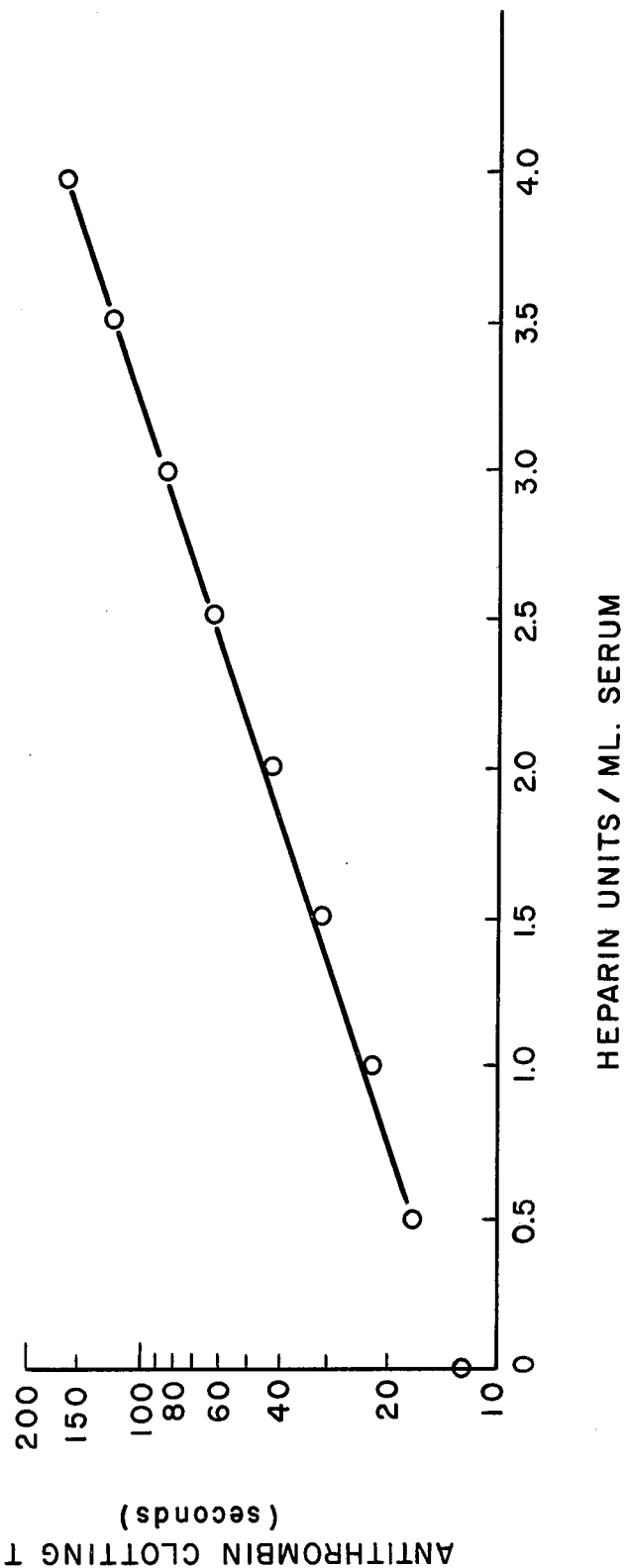

DETERMINATION OF HEPARIN IN THE BLOOD

BACKGROUND OF THE INVENTION

Heparinization is the treatment of choice for a number of pathological conditions. In general, it is critical that the heparin content of the blood be kept within certain limits, these limits depending on a number of variables. However, a major problem in heparin therapy is the absence of a rapid, sensitive technique for determining the concentration thereof in the blood. This situation prevails despite the fact that heparin has been used as an anticoagulant for over 30 years.

At the present time classical laboratory control depends upon the clotting time of whole blood or the activated partial thromboplastin time (APTT). Results are usually expressed as clotting times rather than as units of heparin in the circulating blood. Obviously, it is the latter quantity which is critical and which must serve as the basis for deciding how to proceed with further heparin therapy.

As is evident, a rapid, sensitive and reliable technique for determining heparin concentration would be highly desirable.

SUMMARY OF THE INVENTION

A specimen of blood is drawn from the patient and serum is derived therefrom by the usual clotting and centrifugation technique, after which the serum is incubated at 37° C for ½ hour, prior to use.

Human thrombin is dissolved in saline solution and diluted with isotonic saline until 0.1 ml of the diluted thrombin clots 0.2 ml of fresh normal plasma at 37° C in 12 seconds.

To carry out a test, 0.2 ml of fresh normal plasma are introduced into a glass tube and placed in a water bath to equilibrate at 37° C. 0.1 ml of test serum are added to 0.9 ml of standardized thrombin, mixed thoroughly and placed in a 37° C water bath and kept there for exactly 2 minutes. At the end of 2 minutes, 0.1 ml of the thrombin-serum mixture are added forceably, that is, under conditions such as to mix the solutions thoroughly, to the tube containing 0.2 ml of plasma which has been equilibrated at 37° C. Immediately before or immediately after carrying out this addition, the tube is removed from the bath. The clotting time is then noted.

As a basis for the functional relationship between clotting time and heparin content, serum from a number of normal individuals was treated in vitro with different quantities of heparin. The clotting times were determined as above. The validity of the results derived by the in vitro calibration was established by heparinizing patients with known quantities of heparin, calculating out the concentration of heparin in the blood to be expected on the basis of the patient's weight, and then drawing blood samples for tests by the above method, the blood samples being drawn over a period short enough so that a decrease in concentration of the heparin in the blood was not to be expected. The correlation between the clotting times on the in vitro specimens and those taken from the freshly-heparinized patients was satisfactory.

Accordingly, an object of the present invention is a rapid, reliable and accurate method of determining the heparin content in the blood of a patient.

Another object of the present invention is a rapid, reliable and accurate test for determining the heparin concentration of the blood under conditions such that the relationship between the heparin content and the concentration of anti-thrombin III can be drawn.

Still other objects and advantages of the invention will in part be obvious and will in part be apparent from the specification.

The invention accordingly comprises the several steps and the relation of one or more of such steps with respect to each of the others thereof, which will be exemplified in the method hereinafter disclosed, and the scope of the invention will be indicated in the claims.

BRIEF DESCRIPTION OF THE DRAWING

For a fuller understanding of the invention, reference is had to the following description taken in connection with the accompanying drawing, in which:

The single FIGURE is a graph of clotting time versus concentration of heparin in the blood when the clotting time is measured in accordance with the present invention.

DESCRIPTION OF THE PREFERRED EMBODIMENTS

The method of determining the clotting time of serum, and thereby the concentration of heparin in the blood, is a modification of that disclosed in applicant's U.S. Pat. No. 3,985,618, the contents of said patent being incorporated herein by reference as though presented in their entirety. To carry out the test of the present invention, reagents are prepared as follows:

THROMBIN SOLUTION

Topical thrombin is available from Ortho Diagnostic under the name of Fibrindex. The thrombin is reconstituted by dissolving 50 units in 1 ml of saline solution and then standardized by diluting with isotonic saline until 0.1 ml of the diluted thrombin solution clots 0.2 ml of fresh normal plasma at 37° C in 12 seconds.

PLASMA SOLUTION

A standardized stock solution of plasma is prepared by adding 48 mg of Warner-Lambert plasma to 5 ml of normal saline. It is the fibrinogen content of said plasma which is the active constituent.

TEST SERUM

Test serum is prepared from a blood specimen by the usual clotting and centrifugation procedures. Prior to use, the serum is incubated for ½ hour at 37° C.

CALIBRATION PROCEDURE

A stock aqueous heparin solution having an anticoagulant activity of 5,000 units per ml was used. Serum from 5 normal individuals was heparinized in vitro by mixing 1.0 ml aliquots of serum with 0.1 ml of sodium heparin at concentrations such that the serum samples contained respectively 0.5, 1.0, 1.5, 2.0, 2.5, 3.0, 3.5 and 4.0 units of heparin. The serum heparin concentrations were calculated after correcting for hematocrit.

For each test, 0.2 ml of fresh, normal plasma was pipetted into a glass tube and placed in a water bath at 37° C. Into a second tube was pipetted 0.9 ml of standardized thrombin. From the serum specimen, 0.1 ml were added to the thrombin tube, the contents were mixed thoroughly, and the tube was placed in the water bath at 37° C and kept there for exactly 2 minutes. At the end of the 2 minutes of incubation, 0.1 ml of the thrombin-serum mixture were added forcibly to the tube containing 0.2 ml of plasma which had been equilibrated at 37° C, the addition being carried out under conditions such as to insure good mixing. Essentially at the same time, the tube containing the plasma was removed from the bath and a stop-clock was started. The clotting time was then recorded.

To insure that the tests made on the serum samples which had been heparinized in vitro were meaningful with respect to blood specimens taken from a heparinized patient, test results on such specimens from a heparinized patient were compared with the concentrations of heparin in the circulating blood in the patient expected on the basis of the quantity of heparin added and the quantity of serum calculated on the basis of body weight. It is generally assumed that the total serum volume in milliliters constitutes 5% of the body weight in grams. Consequently the theoretical initial peak of serum heparin concentration can be calculated according to the equation:

$$\text{Serum Heparin Concentration } (\mu/\text{ml}) = \frac{\text{Dose of Heparin in } \mu}{\text{Body weight in grams} \times 0.05}$$

Actually, tests have shown that the heparin concentration of the blood remains constant for a period of perhaps ½ hour after injection. Tests on the serum of heparinized patients correlated well with the results obtained on testing the serum which had been heparinized in vitro.

It should be noted that the serum taken from a patient is stable for about 8 hours at room temperature, so that any tests for heparin therein should be carried out within this period.

To establish the utility of the present test, the APTT test was also run. Plasma for this test was prepared from citrated blood (one part 3.8% trisodium citrate to 9 parts blood). The plasma was defibrinated by heating for 5 minutes at 56° C. The test was carried out according to the procedure of Spector and Corn. Results of both the APTT tests and tests in accordance with the present invention, indicated as AA, are presented in Table I.

TABLE I
IN VITRO CHANGES PRODUCED BY HEPARIN
IN SERUM OF NORMAL SUBJECTS

| Number of Subject Samples | Heparin Units/ml | APTT (Seconds) | AA (Seconds) | Standard Deviation of AA | Antithrombin III (%) |
|---|---|---|---|---|---|
| 5 | 0.5 | 118 (87–147) | 17 (17–18)* | 0.2 | 94 |
|  | 1.0 | 250+ (271–>300) | 23 (21–24) | 1.2 | N.C. |
|  | 1.5 | >300 | 31 (29–34) | 2.4 | N.C. |
|  | 2.0 | >300 | 41 (38–45) | 3.1 | N.C. |
|  | 2.5 | >300 | 61 (57–68) | 4.6 | N.C. |
|  | 3.0 | >300 | 84 (77–84) | 5.9 | N.C. |
|  | 3.5 | >300 | 117 (112–127) | 7.3 | N.C. |
|  | 4.0 | >300 | 169 (151–182) | 9.6 | N.C |

*Ranges in parentheses.
N.C. = No Change

The Antithrombin III concentration was measured in each of the specimens by the immunoassay method according to Fagerhof and Abildgaard.

The single FIGURE shows the experimental results obtained for the serum samples heparinized in vitro, with the heparin concentration in u/ml plotted against the log of the clotting time in seconds. Surprisingly, there is a linear relationship between the log of the clotting time and the heparin concentration over a range from 0 to 4.0 units per ml.

Consideration has been given to factors which may interfere with the clotting time results which are considered to be a measure of the antithrombin concentration. One factor which has already been noted is the sampling time in relation to the heparin dosage. The antithrombin assay follows closely the exponential decay curve of heparin after a plateau which lasts for 30–45 minutes after injection of heparin. Consequently, in calibration of the procedure, it is necessary that blood specimens be taken no later than 30 minutes after injection of heparin. The second factor is the presence of anticoagulant fibrin degradation products (FDP) X and Y in the blood. It is for this reason that the incubation period is kept short, namely two minutes, as against the procedure given in my U.S. Pat. No. 3,853,710 which specifies an incubation period of 15 minutes at 37° C. However, the procedure in said patent is specifically directed to determining the concentration of fibrin degradation products in the blood. The 2-minute incubation period of the present invention merely serves to bring the specimen up to temperature in preparation for reaction with plasma, little if any reaction with the FDP occurring during the 2-minute period.

Fragments D and E are not thrombin-reactive, but although they may impair fibrin polymerization, their effects upon the assay of the present invention is negligible. Applicant has found that patients with thromboembolic disease have significantly depressed assays, thereby eliminating concern about interference of fragments X and Y in heparin assays in these patients, since these fragments would cause lengthening of the clotting time.

The major advantages of the antithrombin assay or AA test of the present invention over the APTT test are twofold. The first is that the relationship between the AA log clotting time and the heparin concentration remains linear at least up to 4 units of heparin per milliliter. The heparin concentration, moreover, can be expressed in terms of heparin unit per milliliter of the serum or plasma, rather than imprecise clotting times. The second advantage is that differences in clotting times can be determined up to levels as high as 4.0 u/ml by the present test whereas by the APTT test, the results, as can be seen from Table I, must be expressed as over 300 seconds. In other words, the APTT test breaks down once the heparin concentration reaches a level of 1.5 u/ml.

According to Pitney, antithrombin activity is the basis for the anticoagulant effect of heparin. The participation of a heparin-antithrombin III (heparin co-factor) complex in heparin anticoagulant action is well documented. Rosenberg and Rosenberg in Current Therapeutic Research 18 No. 1, 66 (1975) showed recently that thrombin inhibition by antithrombin III relates to formation of a strong covalent bond with the active site serine residue on the light subunit chain of thrombin by antithrombin. He further shows that the addition of heparin to this thrombin-antithrombin reaction mixture "dramatically" accelerated the rate of interaction. In similar fashion, it is likely that heparin-antithrombin inhibits other serine proteases, including plasmin and activated factors XI, IX, and X.

In the light of the observations of the Rosenbergs, an important consideration is how much heparin is complexed with antithrombin III at any given time. From the results given in Table I, it is evident that heparinized subjects with marked increases in heparin concentration did not demonstrate increases in anti-thrombin III. The augmented heparin effect, therefore can be ascribed to the heparin component of the heparin-antithrombin III complex. Consequently, it appears that, in heparinized individuals, AA is a quantitative measure of the heparin molecules bound to antithrombin III.

APTT are sensitive indicators of small amounts of circulating heparin, but according to Marder, therapeutic doses of heparin in general exceed the measurable limits of the test. This conclusion is substantiated by the results presented in Table I. In the Marder modification of APTT the plasma is diluted to reduce the heparin concentration to a measurable range. In contrast, when using the present test, namely AA, the undiluted serum can be used and, in addition, there is a linear relationship between the log of the antithrombin clotting time and the heparin concentration from 0 up to 4.0 units per milliliter.

It is emphasized that the concentrations of the various reagents used as well as the temperature and times of incubation can be varied over substantial ranges, if desired. It is only necessary to determine clotting times by the method of in vitro heparinization as aforenoted. Such determination would be well within the ability of one skilled in the art. The temperature of 37° C is specified for incubation due to the fact that most biological laboratories carry out procedures at this temperature, and consequently have such a bath available. In short, applicant's invention is not to be limited by the specific concentrations, temperature and times specified.

It will thus be seen that the objects set forth above, among those made apparent from the preceding description, are efficiently attained and, since certain changes may be made carrying out the above method without departing from the spirit and scope of the invention, it is intended that all matter contained in the above description shall be interpreted as illustrative and not in a limiting sense.

It is also to be understood that the following claims are intended to cover all of the generic and specific features of the invention herein described, and all statements of the scope of the invention, which, as a matter of language, might be said to fall therebetween.

What is claimed is:

1. A method of determining the concentration of heparin in blood in heparinized patients, comprising the steps of equilibrating normal human plasma at a selected temperature, adding serum from said blood to standardized thrombin solution and incubating the resultant thrombin-serum mixture at said selected temperature and for a selected period, said period at said selected temperature being such as to be too brief for substantial reaction between said thrombin and any fibrin degradation products in said serum while sufficient for reaction of heparin with said thrombin, adding a standard portion of said incubated thrombin-serum mixture to said plasma under conditions such as to produce an essentially uniform thrombin-serum-plasma mixture, observing the clotting time thereof, said clotting time being an inverse function of the quantity of thrombin remaining after reaction with said heparin and thereby a direct function of the concentration of heparin in said blood, and comparing the thus-determined clotting time with a curve prepared by adding different quantities of heparin to serum specimens taken from healthy individuals to form heparin-serum solutions, adding each heparin-serum solution to thrombin solution and incubating for said selected period at said selected temperature, adding the incubated heparin-serum-thrombin solution to normal plasma incubated at said selected temperature and noting the clotting time, thereby determining clotting times as a function of heparin content of serum, thus making it possible to specify the heparin content of a patient's blood by measuring the clotting time of serum taken from the blood of said patient.

2. The method as defined in claim 1, wherein the temperature of equilibration of said plasma and incubation of said thrombin-serum mixture is 37° C.

3. The method as defined in claim 1, wherein said thrombin solution is prepared by reconstituting solid thrombin and diluting same until 0.1 ml of the diluted thrombin solution when mixed with 0.2 ml of fresh normal plasma at 37° C has a clotting time of 12 seconds.

4. The method as defined in claim 1, wherein said serum is prepared by normal clotting and centrifugation followed by incubation at 37° C for ½ hour.

5. The method as defined in claim 2 wherein the time of incubation of said thrombin-serum mixture is 2 minutes.

6. A method of determining the concentration of heparin in blood in heparinized patients, comprising the steps of equilibrating normal human plasma at a selected temperature, adding serum from said blood to standardized thrombin solution and incubating the resultant thrombin-serum mixture at said selected temperature for a selected period long enough to bring said thrombin-serum mixture essentially to said selected temperature, adding a standard portion of said incubated thrombin-serum mixture to said plasma under conditions such as to produce an essentially uniform thrombin-serum-plasma mixture, observing the clotting time thereof, said clotting time being an inverse function of the quantity of thrombin remaining after reaction with said heparin and thereby a direct function of the concentration of heparin in said blood, and comparing the thus-determined clotting time with a curve prepared by adding different quantities of heparin to serum specimens taken from healthy individuals to form heparin-serum solutions, adding each heparin-serum solution to thrombin solution and incubating for said period at said selected temperature, adding the incubated heparin-serum-thrombin solution to normal plasma incubated at said selected temperature and noting the clotting time, thereby determining clotting times as a function of heparin content of serum, thus making it possible to specify the heparin content of a patient's blood by measuring the clotting time of serum taken from the blood of said patient.

* * * * *